United States Patent
Okafuji et al.

(10) Patent No.: US 8,828,225 B2
(45) Date of Patent: Sep. 9, 2014

(54) POLYSULFONE HEMODIALYZER

(75) Inventors: Hajime Okafuji, Oita (JP); Satoshi Uezumi, Oita (JP); Makoto Fukuda, Hyogo (JP); Miwa Kawano, Oita (JP); Maho Torii, Tokyo (JP); Masaichi Yamada, Chiba (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 1027 days.

(21) Appl. No.: 11/573,094

(22) PCT Filed: Jul. 22, 2005

(86) PCT No.: PCT/IB2005/002134
§ 371 (c)(1),
(2), (4) Date: Feb. 2, 2007

(87) PCT Pub. No.: WO2006/024902
PCT Pub. Date: Mar. 9, 2006

(65) Prior Publication Data
US 2008/0237127 A1 Oct. 2, 2008

(30) Foreign Application Priority Data

Aug. 6, 2004 (JP) .................. 2004-231131
Sep. 29, 2004 (JP) .................. 2004-284647

(51) Int. Cl.
*B01D 63/00* (2006.01)
*B01D 69/08* (2006.01)
*A61M 1/16* (2006.01)
*B01D 63/02* (2006.01)
*B01D 71/68* (2006.01)

(52) U.S. Cl.
CPC ............ *B01D 63/02* (2013.01); *B01D 2313/14* (2013.01); *B01D 71/68* (2013.01); *B01D 69/084* (2013.01); *A61M 1/16* (2013.01); *B01D 63/022* (2013.01)

USPC ............ 210/321.6; 210/321.61; 210/321.79; 210/500.23; 210/645; 210/646

(58) Field of Classification Search
CPC ..... A61M 1/16; B01D 2313/14; B01D 63/02; B01D 63/022; B01D 69/084; B01D 71/68
See application file for complete search history.

(56) References Cited

U.S. PATENT DOCUMENTS 4,396,510 A    8/1983 Hsei
5,851,394 A *  12/1998 Shibata et al. ........... 210/500.23

(Continued)

FOREIGN PATENT DOCUMENTS

DE    19782098      11/1999
EP    0 306 613  *  3/1989  ............. 210/645

(Continued)

OTHER PUBLICATIONS

Leypoldt et al., Hemodialyzer mass transfer-area coefficients for urea increase at high dialysate flow rates, 1997, Kidney Internatioanl, vol. 51, pp. 2013-2017.*
Depner et al., Assessing adequacy of hemodialysis: Urea modeling, 1994, Kidney International, vol. 45, pp. 1522-1535.*

(Continued)

*Primary Examiner* — Dirk Bass
(74) *Attorney, Agent, or Firm* — Greenblum & Bernstein, P.L.C.

(57) ABSTRACT

An object of the present invention is to provide a polysulfone hemodialyzer with large membrane area that exhibits an unprecedented high dialytic performance over a wide molecular weight range from urea to $\beta_2$-microglobulin. There is provided a polysulfone hemodialyzer having a membrane area of >2.4 but ≤3.2 m² and a dialysate rectifying portion with specified broadening at end portion of bundle, the polysulfone hemodialyzer achieves the above object.

17 Claims, 3 Drawing Sheets

(56) References Cited

U.S. PATENT DOCUMENTS

| | | | |
|---|---|---|---|
| 2003/0155294 A1* | 8/2003 | Heilmann et al. | 210/500.23 |
| 2004/0149645 A1 | 8/2004 | Sunohara et al. | |
| 2004/0206692 A1 | 10/2004 | Oishi et al. | |
| 2004/0247682 A1 | 12/2004 | Sugaya et al. | |
| 2007/0007193 A1* | 1/2007 | Uchi et al. | 210/321.79 |

FOREIGN PATENT DOCUMENTS

| | | |
|---|---|---|
| EP | 0682269 | 11/1995 |
| EP | 1410839 | 4/2004 |
| EP | 1433490 | 6/2004 |
| EP | 1634639 | 3/2006 |
| JP | 53-031828 | 3/1978 |
| JP | 57-053564 | 11/1982 |
| JP | 63-56044 | 4/1988 |
| JP | 3-178667 | 8/1991 |
| JP | 5-115549 | 5/1993 |
| JP | 7-037700 | 2/1995 |
| JP | 7-289863 | 11/1995 |
| JP | 8-246283 | 9/1996 |
| JP | 9-070524 | 3/1997 |
| JP | 11-090186 | 4/1999 |
| JP | 2961481 | 8/1999 |
| JP | 11-332979 | 12/1999 |
| JP | 2000-296318 | 10/2000 |
| JP | 2001-070759 | 3/2001 |
| JP | 2001-309974 | 11/2001 |
| JP | 2002-143298 | 5/2002 |
| JP | 2003-265934 | 9/2003 |
| JP | 2004-154772 | 6/2004 |
| JP | 2005000783 | 1/2005 |
| JP | 2005-152295 | 6/2005 |
| WO | 98/22161 | 5/1998 |
| WO | 98/52683 | 11/1998 |
| WO | 01/60477 | 8/2001 |
| WO | 03/031533 | 4/2003 |
| WO | 2004/058385 | 7/2004 |
| WO | WO2004/094047 | 11/2004 |
| WO | WO2005/044339 | 5/2005 |

OTHER PUBLICATIONS

Shibata, (Referred to in Office Action by assignee SCITEC) Machine Translation of WO 98/022161.*
English Language Abstract of JP 2000-296318.
English Language Abstract of JP 3-178667.
English Language Abstract of JP 2001-070759.
English Language Abstract of JP 7-289863.
English Language Abstract of JP 2002-143298.
English Language Abstract of JP 9-070524.
English Language Abstract of JP 11-332979.
English Language Abstract of JP 7-037700.
English Language Abstract of JP 5-115549.
English Language Abstract of JP 2961481.
English Language Abstract of JP 8-246283.
English Language Abstract of JP 2005-152295.
English Language Abstract of JP 2004-154772.
English Language Abstract of JP 11-090186.
English Language Abstract of JP 2003-265934.
English Language Abstract of JP 2001-309974.
Kidney and Dialysis, High-performance membrane, 2004, pp. 33-36, Tokyo Igakusha Ltd., accompanied by a partial English translation.
Extended European Search Report dated Mar. 4, 2010 that issued with respect to patent family member European Patent Application No. 05768322.9.
Japanese Official Action mailed May 11, 2011 that issued with respect to patent family member Japanese Patent Application No. 2006-530991.
English translation of claims from JP 63-56044, published Apr. 14, 1988.
Ronco et al., "Effects of a reduced inner diameter of hollow fibers in hemodialysers," Kidney International, vol. 58, pp. 809-817 (2000).
German Opposition Statement in counterpart application No. EP20050768322 (with English-language translation) dated Jun. 25, 2013.

* cited by examiner (a)

(b)

POLYSULFONE HEMODIALYZER

TECHNICAL FIELD

The present invention relates to a hemodialyzer filled with polysulfone hollow fiber membranes which is used for hemodialysis, hemofiltration, or hemodiafiltration in the treatment of renal failure. More particularly, the present invention relates to a polysulfone hemodialyzer with a large membrane area which exhibits excellent solute removal performance over a wide molecular weight range even under use conditions in which a high blood flow rate or a high dialysate flow rate is employed.

BACKGROUND ART

When partial or complete dysfunction of the kidney has occurred, wastes which must be excreted from the body as urine accumulate in the blood, and the electrolyte balance in the body is lost. As a method of remedying such renal failure symptoms, an extracorporeal circulation therapy using a hemodialyzer has been widely conducted in which wastes in blood are excreted from the body utilizing the diffusion/filtration principle and the electrolyte balance is adjusted.

A hemodialyzer is produced by incorporating a dialysis membrane in a housing and shaping the dialysis membrane so that mass transfer occurs between the blood and the dialysate through the dialysis membrane. Two compartments of a blood side compartment and a dialysate side compartment are formed in the housing through the dialysis membrane. The hemodialyzers are classified into a flat membrane type and a hollow fiber membrane type. At present, the hollow fiber membrane hemodialyzers are mainly used in which a tubular housing is filled with a hollow fiber membrane bundle and subjected to potting by providing a resin layer portion on each end of the hollow fiber membrane bundle. This is because the hollow fiber membrane hemodialyzer has a large contact area with blood and the dialysate in spite of its small volume as a whole to exhibit excellent mass transfer efficiency.

Various materials ranging from cellulose polymers to synthetic polymers are used for hollow fiber membranes utilized for hemodialyzers. In recent years, a polysulfone polymer has been mainly used as the membrane material since a membrane which shows excellent physical chemical stability and biological safety and exhibits a sharp molecular weight fractionation capability and excellent biocompatibility is easily obtained. However, since the surface of the resulting membrane exhibits too high a hydrophobicity when using only the polysulfone polymer, a small amount of hydrophilic polymer is practically used in combination with the polysulfone polymer. When using the two-component (multicomponent) membrane material prepared by adding the hydrophilic polymer to the polysulfone polymer, various hollow fiber membranes can be formed by adjusting the membrane forming conditions. This also makes the polysulfone polymer preferred as the membrane material.

Hemodialyzers with a blood contact membrane area of 0.1 $m^2$ to 2.5 $m^2$ are commercially available.

In dialysis facilities, a hemodialyzer with an optimum membrane area is selected from them depending on the physique, pathologic condition, treatment conditions, and the like of the target patient and used. Along with a demand for optimization of the treatment conditions and a further increase in the treatment efficiency, a hemodialyzer with a larger membrane area than conventional has been increasingly demanded in order to deal with various physiques of hemodialysis patients. In particular, a hemodialyzer with a large membrane area tends to be strongly demanded in Western countries because dialysis patients have a large physique on average. This is because a hemodialyzer with a large membrane area is suitable for the treatment of a dialysis patient who has a big physique and a large circulation blood volume, and certain treatment effects are expected to be achieved in a shorter period of time than conventional by causing blood or the dialysate to flow at a high flow rate.

However, the membrane areas of hemodialyzers with a large membrane area which have been put to practical use and are available as various products are limited to 2.2 $m^2$ or less. As hemodialyzers with a membrane area exceeding 2.2 $m^2$, only a cellulose triacetate hemodialyzer with a membrane area of 2.5 $m^2$ and a polyarylethersulfone hemodialyzer with a membrane area of 2.4 $m^2$ have been known. Furthermore, it is well known that the membrane material for the former hemodialyzer exhibits poor biocompatibility in comparison with the polysulfone. According to the finding of the inventors of the present invention, the latter hemodialyzer exhibits an insufficient dialysis performance for urea.

The inventors have got suspicious about the fact that polysulfone hemodialyzers with a large membrane area have not been put to practical use in spite of a great demand, and examined the relationship between the membrane area and the dialysis performance of commercially available polysulfone hemodialyzers for solutes with different molecular weights. As a result, the inventors have found that dialysis performance equivalent to the dialysis performance of hemodialyzers with a medium membrane area (about 1.3 to 1.8 $m^2$) cannot be maintained when the membrane area of the hemodialyzer exceeds 2 $m^2$. Uremic toxins with various molecular weights are contained in the blood of a renal failure patient. A hemodialyzer is required to exhibit solute removal capability of reducing all of these uremic toxins. A hemodialyzer is generally required to exhibit capability of removing uremic toxins ranging from urea with a molecular weight of 60 to $\beta_2$-microglobulin with at least a molecular weight of 11,800 as much as possible. According to the finding of the inventors, however, the balance of the dialysis performance is significantly lost when the membrane area exceeds 2 $m^2$. One hemodialyzer (crimped polysulfone hollow fiber membranes, peripheral type baffle with slits) exhibited excellent dialysis performance for $\beta_2$-microglobulin with a high molecular weight, but exhibited insufficient dialysis performance for urea. Another hemodialyzer (spacer fibers twining polysulfone hollow fiber membranes, peripheral type baffle with sloping slits) exhibited excellent dialysis performance for vitamin $B_{12}$ which is a medium molecular weight marker, but exhibited insufficient dialysis performance for urea. Yet another hemodialyzer (spacer fibers twining polyarylethersulfone hollow fiber membranes, peripheral type baffle) also exhibited insufficient dialysis performance for urea.

As described above, a tendency was observed in which it is difficult for polysulfone hemodialyzers to exhibit excellent dialysis performance over the molecular weight range of about 100 to 10,000 when the membrane area exceeds about 2 $m^2$. Urea is the representative substance of uremic toxins and should be removed by a hemodialyzer. However, a polysulfone hemodialyzer with a membrane area exceeding 2 $m^2$ exhibits insufficient dialysis performance for urea. It is considered that this point is one of the technical reasons which prevent a further increase in the membrane area.

The dialysis performance of the hemodialyzer is basically determined by the substance permeability of the individual hollow fiber membranes regardless of the membrane material. However, when several thousands of hollow fiber membranes are bound and filled in the hemodialyzer, a portion in which the dialysate does not sufficiently reach the surfaces of the membranes occurs in the hemodialyzer, whereby a non-uniform flow of the dialysate occurs. As a result, the hemodialyzer always suffers from a problem in which the individual hollow fiber membranes cannot maximally exhibit their inherent substance permeability. Therefore, it is necessary to improve and optimize the structure of the hemodialyzer in addition to the permeability of the dialysis membrane.

A number of studies have been conducted on the structure of the hemodialyzer for improving the dialysis performance in terms of the shape of the bundle, the shape of the housing, or the entire shape including the bundle.

Regarding the entire shape including the bundle, attempts have been made to increase the length of the housing with respect to the diameter of the housing. For example, patent documents 1 and 2 disclose technologies of improving the dialysis performance by increasing the ratio (L/D) of the length (L) and the diameter (D) of the housing. Patent document 3 discloses technology of increasing the ratio (L/D) by providing a swellable member which reduces the diameter of the major portion of the bundle in the housing.

However, when the membrane area is increased by the method of increasing the ratio (L/D) as disclosed in the patent documents 1 and 2, the length of the hemodialyzer must be increased. This increases the blood side and dialysate side pressure drop, whereby incensing the risk that the dialysate contaminant likely flows into the blood side due to hemolysis or reverse filtration. Though the diameter of the major portion of the bundle is reduced as disclosed in the patent document 3, reverse filtration of the dialysate increasingly occurs. Although the removal performance for proteins such as $\beta_2$-microglobulin is improved, an improvement in the dialysis performance for low-molecular-weight solutes such as urea is not recognized.

Regarding the shape of the bundle, attempts have been made to provide a certain space between the hollow fiber membranes so that the hollow fiber membranes in the bundle do not adhere each other to form a dialysate channel. For example, patent document 4 discloses technology of preventing adhesion between the hollow fiber membranes by regularly twining spacer fibers around the hollow fiber membranes to provide a space. Patent documents 5 and 6 disclose technologies of providing a space between the hollow fiber membranes by geometrically crimping the hollow fiber membranes. In particular, the patent document 3 discloses that loading the housing with a bundle subjected to specific winding step reduces a local variation in dialysis performance for myoglobin (molecular weight: about 16,000) in the hemodialyzer, even if the same crimped hollow fiber membranes are used.

However, these technologies result in an increase in the diameter of the bundle or an increase in the size of the hemodialyzer. For example, the blood volume of the header is increased. Moreover, reverse filtration may be increased due to an increase of pressure drop in the dialysate side.

Regarding the shape of the housing, attempts have been made to allow the dialysate introduced through the dialysate inlet port to spread over the entire bundle without being retained or passing through a short path. For example, patent document 7 discloses a peripheral type baffle which is tapered toward the end of the hemodialyzer. The patent document 7 qualitatively demonstrates that the flow of the dialysate can be made uniform when the diameter of the bundle is partially increased along the tapered baffle. Patent documents 8 and 9 and non-patent document 1 disclose peripheral type baffles which generate a slit flow. In particular, the non-patent document 1 discloses that use of a peripheral type baffle provided with slits sloping to the hollow fiber membranes reduces a local variation in dialysis performance for vitamin $B_{12}$ (molecular weight: 1,355) in the dialyzer.

However, any of these technologies complicate the structure of the housing. Moreover, when the diameter of the bundle is significantly increased along with an increase in the membrane area, the dialysate does not seem to reach the center portion of the bundle at a normal dialysate flow rate, for example.

As described above, when improving the shape of the bundle or the shape of the housing in addition to the entire shape, the dialysis performance is improved although some disadvantages occur due to an increase in the diameter of the bundle or a complicated housing structure. Therefore, some technologies have been put to practical use. However, the above technologies are successful for only hemodialyzers with a membrane area of about 1.5 to 1.6 $m^2$. None of the above documents suggests application of the above technologies to hemodialyzers with a large membrane area exceeding 2.4 $m^2$ and an improvement in dialysis performance for low-molecular-weight solutes.

[Patent document 1] JP-UM-B-57-53564
[Patent document 2] Japanese Patent No. 2961481
[Patent document 3] WO98/022161
[Patent document 4] JP-A-08-246283
[Patent document 5] WO01/60477
[Patent document 6] JP-A-2005-152295
[Patent document 7] JP-B-53-31828
[Patent document 8] JP-UM-B-07-37700
[Patent document 9] JP-A-2004-154772
[Non-patent document 1] Kidney and Dialysis (separate volume), High-performance Membrane 2004, pp. 33 to 36, Tokyo Igakusha Ltd

DISCLOSURE OF THE INVENTION

Problems to be Solved by the Invention

The present invention has been achieved aiming at solving the above-described problems which prevent an increase in membrane area of polysulfone hemodialyzers. Specifically, an object of the present invention is to provide a polysulfone hemodialyzer with a large membrane area which exhibits a high dialysis performance in comparison with conventional hemodialyzers over a wide molecular weight range, from urea with a low molecular weight to $\beta_2$-microglobulin with a high molecular weight.

Means for Solving the Problems

The inventors have comprehensively analyzed the findings concerning the membrane area and the dialysis performance of commercially available polysulfone hemodialyzers and the technologies which have been studied concerning an improvement in the dialysis performance. As a result, the inventors have hypothesized that "the flow of the dialysate may be made uniform by using a hollow fiber membrane bundle alone provided with crimps or spacer fibers or using such a hollow fiber membrane bundle together with a certain baffle when the bundle has a diameter which achieves a membrane area of about 2 $m^2$ or less. However, in order to achieve a larger membrane area than that which has been achieved, the diameter of the hemodialyzer must be increased from the viewpoint of pressure drop. In a dialyzer with such a large membrane area, the dialysate does not prevail the center portion of the bundle. Even if a device such as a slit baffle is provided, limitations exist inasmuch as using known crimps or spacer fibers".

The inventors have conducted extensive studies based on the above hypothesis. As a result, the inventors have found that, even if the bundle of the hemodialyzer has a diameter equivalent to that of a hemodialyzer with a large membrane area, it is effective to provide a dialysate rectifying portion near the end of the bundle. Specifically, the inventors have found that a polysulfone hemodialyzer with a large membrane area can be obtained which exhibits a higher dialysis performance than conventional over a wide molecular weight range by forming a three-dimensional structure with a specific expansion in the end portion of the bundle. This finding has led to the completion of the present invention.

Specifically, the present invention includes the following inventions.

(1) A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped, characterizing in that the hemodialyzer has a membrane area of more than 2.4 m$^2$ and 3.2 m$^2$ or less, and the bundle includes a straight portion and a dialysate rectifying portion, a ratio of a dialysate channel area in a diameter-expansion-start portion to a dialysate channel area inside the resin layer portion is 0.2 to 0.5 and the dialysate rectifying portion having a distance from the diameter-expansion-start portion to the inside of the resin layer portion of 10 to 46 mm is provided in a dialysate inlet port side end portion of the bundle.

(2) A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped, characterizing in that the hemodialyzer has a membrane area of more than 2.4 m$^2$ and 3.2 m$^2$ or less, and a urea overall mass transfer coefficient is $9.50 \times 10^{-4}$ cm/sec or more at a blood flow rate of 400 ml/min and a dialysate flow rate of 800 ml/min, and a difference ($Ko_{(C)} - Ko_{(AVE)}$) between a urea center portion overall mass transfer coefficient ($Ko_{(C)}$) and an average urea peripheral portion overall mass transfer coefficient ($Ko_{(AVE)}$) at a blood flow rate of 400 ml/min and a dialysate flow rate of 800 ml/min is $-2.7 \times 10^{-4}$ to $2.5 \times 10^{-4}$ cm/sec.

(3) A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped, characterizing in that the hemodialyzer has a membrane area of more than 2.4 m$^2$ and 3.2 m$^2$ or less, and an overall mass transfer coefficient (Ko) of a solute with a molecular weight (M) at a blood flow rate of 400 ml/min and a dialysate flow rate of 800 ml/min satisfys the following relational, $$Ko > 89.313 \times M^{-0.4865} \ (60 \leq M \leq 9600).$$

Effect of the Invention

The polysulfone hemodialyzer according to the present invention can exhibit a high dialysis performance in comparison with a known hemodialyzer over a wide molecular weight range, from urea with a low molecular weight to $\beta_2$-microglobulin with a high molecular weight, even though the polysulfone hemodialyzer has a large membrane area exceeding 2.4 m$^2$. The polysulfone hemodialyzer according to the present invention can exhibit a high dialysis performance without requiring an additional structure member or an additional structural treatment such as a spacer fiber or crimping or a complicated housing structure such as a slit baffle.

Since the polysulfone hemodialyzer according to the present invention has a large membrane area in comparison with known hemodialyzers, the polysulfone hemodialyzer according to the present invention is suitable for treating a big physique patient who weighs more than 176 pounds, for example. Moreover, desired treatment effects can be obtained in shorter period of time by carrying out dialysis at a higher blood flow rate and a higher dialysate flow rate than conventional.

EXPLANATION OF NUMERALS

Figure 1:
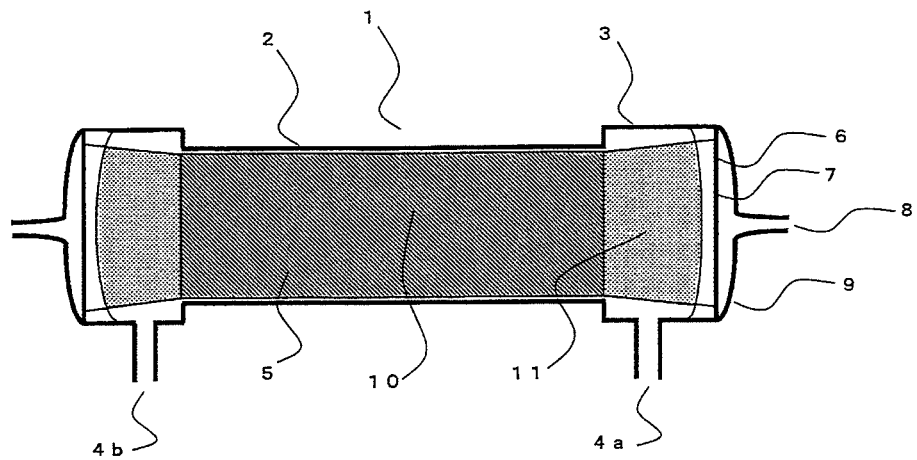
FIG. 1 is a schematic diagram showing the entire structure of a polysulfone hemodialyzer according to the present invention.

1 Tubular housing
2 Body portion
3 Head portion
4a Dialysate inlet port
4b Dialysate outlet port
5 Hollow fiber membrane bundle
6 Open end of hollow fiber membranes
7 Resin layer portion
8 Blood circulation port
9 Header portion
10 Straight portion
11 Dialysate rectifying portion
12 Diameter-expansion-start surface
13 Slope portion
14 Peripheral type baffle
15 Base portion of baffle
16 Opening 17 Groove
18 Virtual cross section including base portion
19 Top portion of baffle
20 Virtual cross section including top portion

BEST MODE FOR CARRYING OUT THE INVENTION

The present invention is described below in detail.

The term "hollow fiber membrane formed from a polysulfone polymer and polyvinylpyrrolidone (hereinafter called "PVP") used in the present invention refers to a hollow fiber membrane including an aromatic polysulfone resin such as polysulfone, polyethersulfone, or polyarylethersulfone as the main component and PVP for mainly hydrophilizing the surface of the membrane. The polysulfone polymer used as the main component is a membrane material which exhibits particularly excellent physical chemical stability and biological safety in comparison with other synthetic polymers and can form various hollow fiber membranes by adjusting the membrane forming conditions. Therefore, a membrane exhibiting a sharp molecular weight fractionation capability and excellent biocompatibility is easily obtained. Moreover, since the polysulfone polymer exhibits excellent resistance property to radiation widely used for sterilization of medical instruments, the polysulfone polymer is most optimum as a membrane material. The detailed composition of the polysulfone polymer, the membrane structure, and the membrane formation method should not be particularly limited. Since the present invention aims at a high-performance hemodialyzer, it is necessary for the hollow fiber membrane to have the following mass transfer coefficients for uremia substances or molecular weight markers thereof as the substance permeability specific to the hollow fiber membrane. Specifically, the hollow fiber membrane exhibits a mass transfer coefficient for aqueous urea (molecular weight: 60) of $8.0 \times 10^{-4}$ cm/sec or more, a mass transfer coefficient for aqueous vitamin $B_{12}$ (molecular weight: 1,355) of $2.0 \times 10^{-4}$ cm/sec or more, and a mass transfer coefficient for plasma $\beta_2$-microglobulin (molecular weight: 11,800) of $0.2 \times 10^{-4}$ cm/sec or more.

Such a hollow fiber membrane may be obtained by referring to WO98/52683, WO2003/9926, and the like, for example.

In the polysulfone hemodialyzer according to the present invention, a tubular housing is filled with a bundle formed by binding about several thousands to several tens of thousands of hollow fiber membranes. The term "membrane area" used herein refers to an internal membrane area calculated from the length, the inner diameter, and the total number of hollow fiber membranes in the effective portion which contributes to substance permeation such as dialysis or filtration. The term "large membrane area" used in the present invention refers to a membrane area exceeding 2.4 m², which is not achieved by conventional polysulfone hemodialyzers. Note that the blood volume inside the hemodialyzer including a blood circuit, that is, the amount of blood brought out from the body during dialysis treatment must be reduced to such an extent that the patient's hemodynamics is not adversely affected. For example, since two hemodialyzers with a membrane area of about 1.5 to 1.6 m² may be connected and used according to some dialysis treatment, the upper limit of the membrane area is set at 3.2 m² based on this finding.

As shown in FIG. 1, the polysulfone hemodialyzer according to the present invention includes a tubular housing 1 which has a straight body portion 2 and head portions 3 positioned on both side of the body portion 2 with a dialysate inlet port 4a provided in one head portion 3 and a dialysate outlet port 4b provided in the other head portion 3, a hollow fiber membrane bundle 5 with which the tubular housing 1 is filled, a resin layer portion 7 provided on the end of the head portion 3, the resin layer portion 7 securing the hollow fiber membrane bundle 5 to the inside of the housing and forming an open end 6 of the hollow fiber membranes, and a header portion 9 which has a blood circulation port 8 and with which the resin layer portion 7 is capped.

The straight body portion 2 is provided with a draft angle of approximately maximum 0.5° for convenience of injection molding in a rigorous manner. Since the effects of such a small variation in shape on the flow of the dialysate can be negligible, the body portion 2 provided with a draft angle is also regarded as straight in the present invention.

The head portion 3 has a diameter greater than that of the body portion 2 so that the dialysate entering through the dialysate inlet port 4a flows over the entire circumference of the bundle in the head portion 3. A baffle may be provided in the head portion 3.

In the present invention, the tubular housing is classified as the body portion 2, the head portion 3, and the header portion 9. This classification is for the sake of convenience. A modification in which the header portion 9 is integrated with the head portion 3 of the tubular housing or the body portion 2 and the head portion 3 of the tubular housing are formed from separate parts is within the scope of the present invention inasmuch as a dialysate rectifying portion described later is provided in the end portion of the bundle.

In the present invention, the loaded bundle includes a straight portion 10 and a dialysate rectifying portion 11. The dialysate rectifying portion has a ratio of the dialysate channel area at the diameter-expansion-start surface to the dialysate channel area inside the resin layer portion of 0.2 to 0.5 and a distance from the diameter-expansion-start surface to the inside of the resin layer portion of 10 to 46 mm and is provided at least in the dialysate inlet port side end portion of the bundle.

Figure 2:
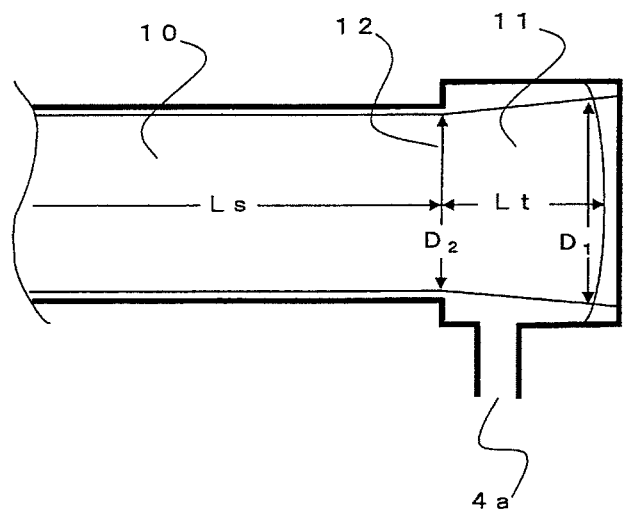
FIG. 2 is a schematic diagram showing a bundle structure of a polysulfone hemodialyzer according to the present invention.

The term "dialysate channel area inside the resin layer portion" used herein refers to an area obtained by subtracting the sum of the cross-sectional areas of the hollow fiber membranes based on outer diameters thereof from the cross-sectional area based on the diameter ($D_1$) of the bundle exposed in a state in which the bundle is partially embedded in the resin layer portion when disassembling the hemodialyzer and cutting the hollow fiber membranes along the curved surface of the resin layer inside the resin layer portion (see equation 1 and FIG. 2). The diameter of the bundle is the average value of the lengths obtained by measuring the distance between the hollow fiber membranes present on the outermost circumference through the central axis using slide gauge or the like at 10 locations or more.

Dialysate channel area inside resin layer portion=$(D_1/2)^2 \times \pi - \{$(outer diameter of hollow fiber membrane/2$)^2 \times \pi \times$number of hollow fiber membranes$\}$ (1)

Figure 3:
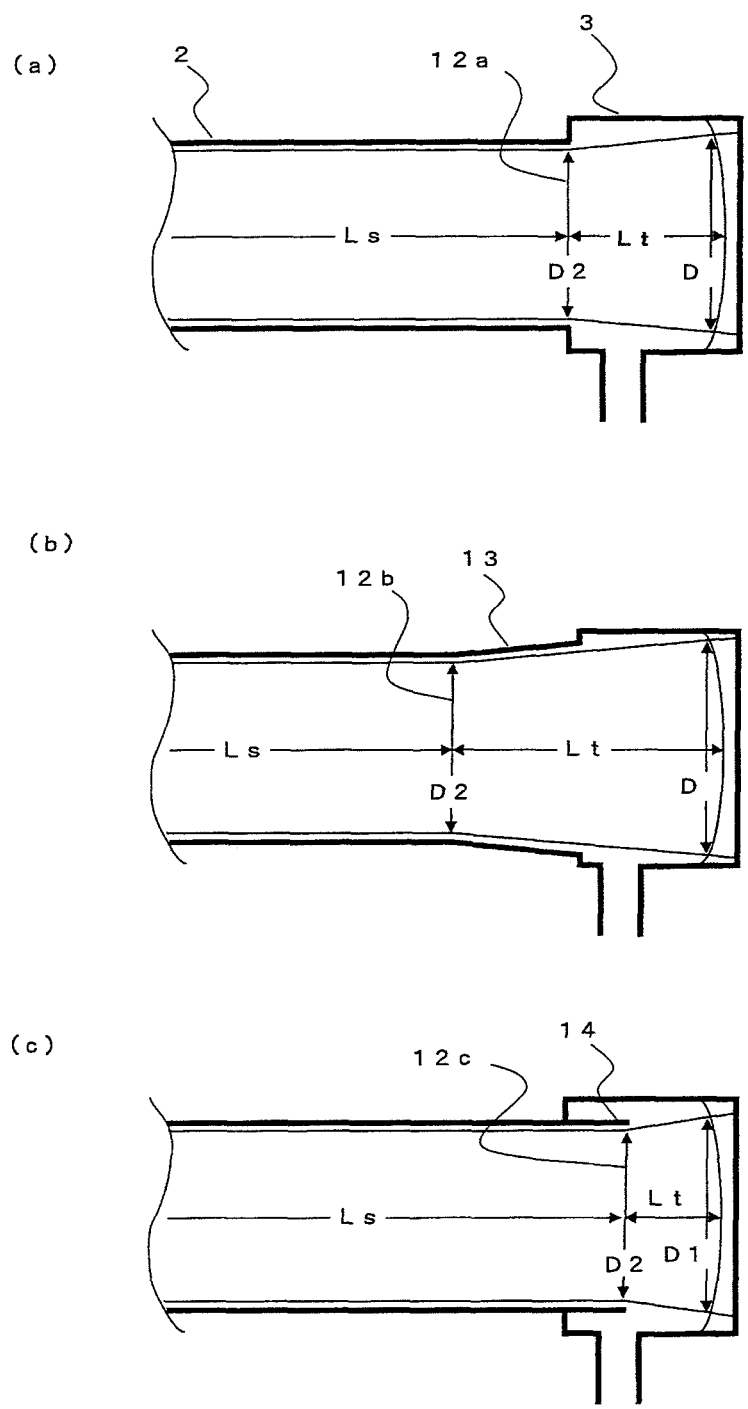
FIG. 3 is a schematic diagram showing variations of the structure near the head portion of a polysulfone hemodialyzer according to the present invention.

The term "dialysate channel area at the diameter-expansion-start portion" refers to the dialysate channel area at the cross section of the bundle at which the diameter of the bundle inside the housing starts to increase from the middle portion toward the end portion. It may be difficult to clearly define the diameter-expansion-start surface of the bundle depending on the degree of diameter expansion or the hollow fiber membranes with or without crimp. In the present invention, the housing is classified into three types indicated by (a) to (c) in FIG. 3, and the diameter-expansion-start surface is defined for each type. Specifically, (a) indicates the case where a baffle is not provided or a tongue-shaped baffle is provided. In this case, a boundary surface 12a between the body portion and the head portion of the tubular housing is defined as the diameter-expansion-start surface. (b) indicates the case where a slope portion 13 is provided between the body portion and the head portion of the tubular housing. In this case, a boundary surface 12b between the body portion and the slope portion of the tubular housing is defined as the diameter-expansion-start surface. (c) indicates the case where a peripheral type baffle 14 is provided in the head portion of the tubular housing and an increase in the diameter of the bundle is inhibited by the baffle. In this case, a cross section 12c at the top of the peripheral type baffle 14 is defined as the diameter-expansion-start surface.

In each case, the diameter of the bundle approximately corresponds to the inner diameter of the housing in general. Therefore, the dialysate channel area at the diameter-expansion-start surface 12 (12a, 12b, 12c) refers to an area obtained by subtracting the sum of the cross-sectional areas of the hollow fiber membranes based on the outer diameter thereof from the cross-sectional area based on the inner diameter ($D_2$) at the diameter-expansion-start surface 12 of the housing (see equation 2 and FIG. 3). When spacer fibers twine around the hollow fiber membranes, the total cross-sectional area of the spacer fibers is further subtracted from the value obtained by the equation 1 and the equation 2.

Dialysate channel area at diameter-expansion-start portion=$(D_2/2)^2 \times \pi$−{(outer diameter of hollow fiber membrane/2)$^2 \times \pi \times$number of hollow fiber membranes} (2)

In the present invention, the ratio of the dialysate channel area at the diameter-expansion-start surface to the dialysate channel area inside the resin layer portion must be 0.2 to 0.5. The dialysate which has entered the housing more easily reaches the center of the bundle as the above ratio becomes smaller. On the other hand, the diameter of the bundle may be unnecessarily increased in the resin layer portion at the same time. This makes it necessary to increase the diameter of the header, whereby the blood volume of the hemodialyzer may be increased. To the contrary, it becomes difficult to secure a space between the hollow fiber membranes near the dialysate inlet port as the above ratio becomes closer to 1, whereby the function of the dialysate rectifying portion cannot be achieved. Or, the diameter of the entire body portion of the tubular housing is unnecessarily increased, whereby the dialysis efficiency is decreased. The above ratio is more preferably 0.3 to 0.4, and particularly preferably 0.33 to 0.38.

In such cases, in order to reduce the header diameter of the hemodialyzer as less as possible to reduce the blood volume, it is preferable to adjust the diameter of the bundle inside the resin layer portion to 60 mm or less.

The term "distance from the diameter-expansion-start surface to the inside of the resin layer portion" means the length of the dialysate rectifying portion. In the present invention, since the diameter-expansion-start surface is defined as indicated in FIG. 3(a) to (c), the distance from the diameter-expansion-start surface to the inside of the resin layer portion refers to the distance (Lt) from the center of the diameter-expansion-start surface to the center inside the resin layer portion. In the present invention, when the ratio of the dialysate channel area at the diameter-expansion-start surface to the dialysate channel area inside the resin layer portion is 0.2 to 0.5, the distance (Lt) must be 10 to 46 mm. If the distance (Lt) is too short, the dialysate which has entered the housing does not sufficiently reach the center of the bundle and is not made uniform while occurring maldistribution flow. To the contrary, if the distance (Lt) is too long, the distance required to make the flow of the dialysate uniform is unnecessarily increased, whereby the length in which the dialysate exhibits a sufficient dialysis performance is reduced. The distance (Lt) is more preferably 20 to 36 mm, and particularly preferably 24 to 30 mm.

In the present invention, the ratio of the length (Ls) of the straight section of the hollow fiber membrane bundle to the length (Lt) of the dialysate rectifying portion provided on the dialysate inlet port side is preferably 3.0 to 10.0. Since the dialysate which has sufficiently reached the center of the bundle in the dialysate rectifying portion fully exhibits its dialysis performance in the straight portion, it is so preferable that the above ratio be greater from the viewpoint of improvement in dialysis performance. However, since it is necessary to appropriately control the pressure drops in the blood side and dialysate side, it is unpreferable to unnecessarily increase the above ratio. The above ratio is more preferably 5.5 to 10.0, and particularly preferably 7.5 to 10.0.

As described above, the dialysate rectifying portion is a portion with a partially conical structure determined by the diameters of both ends and length thereof. The specific shape of the dialysate rectifying portion is not limited. For example, the oblique side of the partial cone may be a straight line, a curve, or a line which is bent in two or more stages.

When bubbles which occur during priming are trapped in the center portion of the bundle on the dialysate outlet port side, since these bubbles are not easily released to the outside, the dialysis efficiency may be locally decreased. The dialysate rectifying portion is necessary at least on the dialysate inlet port side of the bundle. If the dialysate rectifying portion is also provided on the dialysate outlet port side of the bundle, the bubble discharge properties are preferably improved. The shape of the dialysate rectifying portion on the dialysate outlet port side may or may not be symmetrical to that of the dialysate rectifying portion on the inlet port side.

Preferred embodiments in terms of further improving the effects of the dialysate rectifying portion are described below.

In the present invention, though the hollow fiber membrane may be a straight fiber, it is preferable to crimp the hollow fiber membranes or twine spacer fibers around the hollow fiber membranes. This enables the dialysate to more reliably and easily reach the vicinity of the center of the bundle in the dialysate rectifying portion. For example, since the dialysate easily reaches the center of the bundle even if the dialysate flow rate is more reduced than usual as in a dialysate saving mode, an excellent dialysis performance can be exhibited under a wider range of conditions. Moreover, a rectified uniform flow can be maintained over the entire length of the bundle at the same time.

The desired effects can be obtained by either crimping or using the spacer fibers. However, when the hollow fiber membrane has a low flexural strength and the entire bundle is easily bent due to a liquid stream, the hollow fiber membrane bundle may be compressed from the periphery toward the center if the dialysate is caused to flow at a high flow rate. In this manner, when the shape of the entire bundle changes due to a liquid stream, it is difficult to fully achieve the crimping effects due to an increase in adhesion between the hollow fiber membranes, even though crimping is applied. Therefore, it is more effective to twine with the spacer fibers. Specifically, if the spacer fibers twine around the hollow fiber membranes, since a change in the shape of the bundle due to the dialysate flow is suppressed so that the space can be secured between the hollow fibers in an amount corresponding to the diameter of the spacer fiber, an excellent dialysis performance is expected even when used at a high dialysate flow rate of 800 ml/min. The crimp pitch and the crimp amplitude are not particularly limited. For example, the crimp pitch and the crimp amplitude are preferably about 0.1 to 2.0 cm and about 0.2 to 0.8 mm, and more preferably about 0.4 to 0.8 cm and about 0.4 to 0.6 mm, respectively. The spacer fiber is not particularly limited. For example, a spacer fiber and a twining method disclosed in JP-A-8-246283 and the like may be adopted.

In the present invention, in order to increase the substance permeability of the hollow fiber membrane and prevent the size of the hemodialyzer from being unnecessarily increased, it is preferable that the hollow fiber membrane have a small inner diameter and a small thickness. Though the inner diameter of the hollow fiber membrane is generally 200 µm, the inner diameter is preferably 190 µm or less, and more preferably 185 µm or less from the viewpoint of the above objective. However, if the inner diameter of the hollow fiber membrane is too small, a problem such as hemolysis likely occurs due to increase of the pressure drop in the blood side. Therefore, the inner diameter of the hollow fiber membrane is preferably 170 µm or more, and more preferably 175 µm or more taking into consideration the case of causing blood to flow at a high blood flow rate of about 400 ml/min.

The thickness of the hollow fiber membrane is generally about 40 to 50 µm when using the polysulfone polymer. It is preferable that the hollow fiber membrane have a smaller thickness from the viewpoint of the above objective. However, when using a two-component (multicomponent) membrane material formed of a hydrophobic polymer and a hydrophilic polymer, a reduction in thickness may be limited from the viewpoint of tensile strength and flexural strength, differing from a single-component membrane material with high crystamity such as a cellulose or cellulose triacetate hollow fiber membrane. Therefore, the thickness of the polysulfone hollow fiber membrane is preferably 25 µm or more, and more preferably 30 µm or more taking into consideration the maximum service pressure (600 mmHg) generally employed for the hemodialyzer, the maximum blood flow rate (400 ml/min), and the maximum dialysate flow rate (800 ml/min).

In the present invention, it is preferable that PVP included in the hollow fiber membrane be partially insolubilized through crosslinking. A method of partially crosslinking PVP and its effects are disclosed in WO98/52683. Specifically, WO98/52683 describes that PVP can be only partially crosslinked by controlling the irradiation efficiency of radiation applied to the hemodialysis membrane, and the resulting membrane exhibits excellent antithrombogenic properties in comparison with a membrane in which PVP is entirely crosslinked and insolubilized.

Surprisingly, according to the present invention, when PVP is partially crosslinked and insolubilized, an excellent dialysis performance tends to be obtained in a well-balanced manner over a wide molecular weight range. Specifically, this tendency is significant when 50 to 95% of PVP included in the hollow fiber membrane is insolubilized. The reason that the degree of crosslinking of PVP takes part in the dialysis performance may be considered as follows. Specifically, when PVP is almost completely crosslinked, the thickness of the water-containing layer on the surface of the membrane is reduced, whereby a surface structure is formed which exhibits reduced hindrance to protein permeation but is not suitable for permeation of low-molecular-weight solutes such as urea which utilize diffusion as the driving force. On the other hand, when PVP is crosslinked to only a small extent, the thickness of the water-containing layer on the surface of the membrane is increased, whereby a surface structure is formed which is suitable for diffusion of low-molecular-weight solutes but exhibits increased hindrance to protein permeation. Therefore, either system shows a poorly balanced dialysis performance. However, when PVP is only partially crosslinked, a surface structure is formed which exhibits excellent substance permeability over a wide molecular weight range.

In the present invention, it is preferable to adjust the water permeation rate of the hollow fiber membrane to 350 ml/mmHg·hr·m$^2$ or less. The water permeation rate does not directly indicate the pore size of the membrane, but is an index indicating the pore size and the pore size distribution. In general, reverse filtration of the dialysate tends to occur easily when using a membrane with a high water permeation rate, whereby contaminants in the dialysate likely flow into the blood due to reverse filtration. Contrary, if the water permeation rate is too low, the ultrafiltration rate or permeability of low-molecular-weight proteins tends to be decreased, when causing blood to flow. Taking these tendencies and the size of an endotoxin fragment (molecular weight: about 5,000) into consideration, it is preferable that the water permeation rate be 350 ml/mmHg·hr·m$^2$ or less and 100 ml/mmHg·hr·m$^2$ or more. The water permeation rate is more preferably 300 to 150 ml/mmHg·hr·m$^2$. If the water permeation rate is within the above range, the plasma albumin permeation rate tends to be reduced to 0.5% or less, whereby the molecular weight fractionation capability with respect to uremic toxins which must be removed becomes sharp. In particular, it is preferable to combine the water permeation rate within the above range with partial crosslinking of PVP described above since a sharper fractionation capability is achieved.

In the present invention, the shape of the tubular housing which encloses the dialysate rectifying portion is not particularly limited. For example, a large space may be formed between the dialysate rectifying portion and the inner surface of the head portion of the housing, as shown in FIG. 3(a). It is, however, more preferable that the slope portion 13 of the housing be provided along the outer circumference of the dialysate rectifying portion of the bundle, as shown in FIG. 3(b). Such a housing shape allows the dialysate to more easily reach the center of the bundle in the dialysate rectifying portion, and reduces retention of the dialysate in the head portion. The length of the slope portion 13 is preferably 20 to 50% of the length (Lt) of the dialysate rectifying portion.

In the present invention, it is preferable that the filling rate of the hollow fiber membranes in the tubular housing be 55% or more and less than 70%. The filling rate of the hollow fiber membranes in the tubular housing used in the present invention refers to the percentage of the sum of the cross-sectional areas of the hollow fiber membranes based on outer diameter thereof with respect to the cross-sectional area of the body portion of the housing at the minimum inner diameter. Specifically, the filling rate is calculated by the following equation (3).

$$\text{Bundle filling rate}(\%) = 100 \times \{(\text{outer diameter of hollow fiber membrane}/2)^2 \times \pi \times \text{number of hollow fiber membranes}\} / \{(\text{minimum inner diameter of body portion of housing}/2)^2 \times \pi\} \quad (3)$$

If the fling rate is less than 55%, an empty portion tends to be formed in the diametrical direction of the housing to form a short path in which the dialysate easily flows, whereby the dialysate may not uniformly flow. On the other hand, if the filling rate is greater than 70%, reverse filtration of the dialysate is accelerated due to an increase of the pressure drop in the dialysate side. The filling rate is more preferably 56% or more and 69% or less, and still more preferably 58% or more and 68% or less.

In the present invention, it is preferable that a baffle be provided at least on the dialysate inlet port side of the hemodialyzer. On the dialysate inlet port side, the baffle disperses a liquid stream which has entered into the housing around the bundle, and moderates direct collision of a liquid stream with the hollow fiber membranes positioned near the dialysate inlet port. On the other hand, on the dialysate outlet port side, the hollow fiber membranes positioned near the dialysate outlet port can be prevented from being drawn toward the outlet port due to a liquid stream. As described above, the baffle is expected to disperse the dialysate around the bundle and prevent damage to the membranes by the liquid stream.

The shape of the baffle is not particularly limited. The baffle may be a tongue-shaped baffle which is provided to face only the portion in which the dialysate inlet port or outlet port is open toward the inner circumferential surface of the head portion, or may be a peripheral type baffle which surrounds the circumference of the end portion of the bundle. It is preferable to use the peripheral type baffle since the hollow fiber membranes in the outer circumferential portion of the bundle can be protected over the entire circumference by optimizing the width of the space between the top portion of the baffle and the inside of the resin layer portion. It is particularly preferable that the inner circumferential surface of the peripheral type baffle be gradually increased in diameter from the base portion toward the top portion of the baffle along the shape of the dialysate rectiying portion of the bundle including the following examples.

As examples of the peripheral type baffle with a special shape, baffles with a slit disclosed in JP-UM-B-07-37700 and JP-A-2004-154772 have been known. In these baffles, a plurality of slits parallel to or at a certain angle with the hollow fiber membranes are provided over the entire circumference in a state in which the entire circumference of the top portion of the baffle reaches the resin layer portion. According to such a structure, since the dialysate which has entered into the head portion of the housing forms a slit flow almost parallel to the hollow fiber membranes through the slits, the resistance of the bundle is reduced, whereby the dialysate easily pervades over from the circumference to the center of the bundle. In particular, the diagonal slit is suitable for a dialysate flow at a high flow rate and optimum for use in the hemodialyzer according to the present invention.

Figure 4:
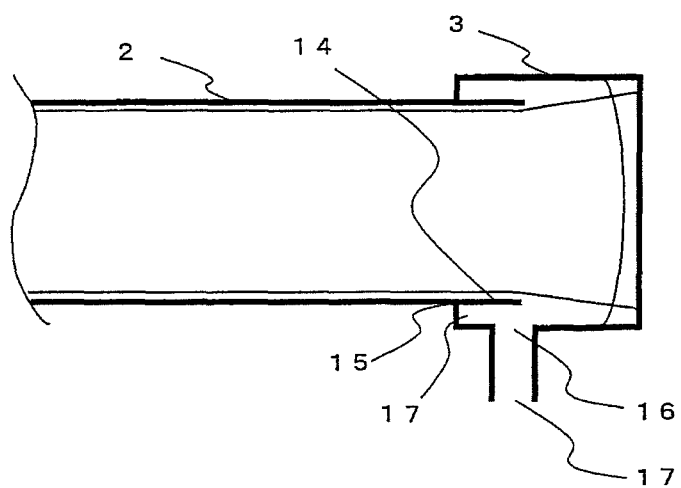
FIG. 4 is a schematic diagram showing examples of the structure near the head portion of a polysulfone hemodialyzer according to the present invention.
Figure 4:
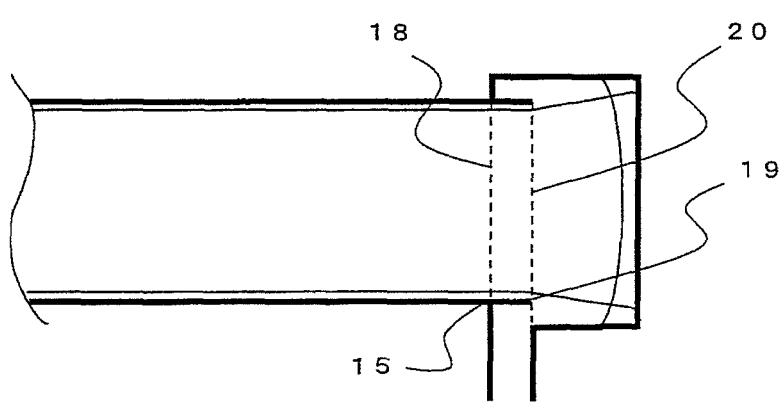

When using the peripheral type baffle, the positional relationship between the baffle and the dialysate inlet port may considerably affect the dialysis performance. As shown in FIG. 4(a), the baffle 14 generally has a base portion 15 at the boundary between the body portion and the head portion of the housing, and is provided to face a portion 16 in which the dialysate inlet port or outlet port is open toward the inner circumferential surface of the head portion. A groove 17 surrounded by the outer circumferential surface of the baffle, the base portion 15, and the inner circumferential surface of the head portion becomes larger as the base portion 15 of the baffle is displaced from the opening 16 toward the body portion. In this case, since the groove 17 functions as a retention portion for the dialysate to reduce the force of the infalling dialysate, the dialysate does not sufficiently reach the center of the bundle, whereby the dialysis performance is decreased. This significantly occurs in a hemodialyzer with a large diameter. Therefore, it is preferable to minimize the groove 17 by reducing the difference in position between the base portion 15 of the baffle and the opening 16. As shown in FIG. 4(b), it is preferable to position a virtual cross section 18 including the base portion 15 of the baffle to contact the body portion side circumferential portion of the opening 16 since such a groove is eliminated. In this case, it is particularly preferable to form a slope or an angle from the vicinity of the base portion of the outer circumferential surface of the baffle to the inside of the dialysate inlet port since the flow of the infalling dialysate in the direction of the resin layer portion is enhanced.

It is also preferable to position a virtual cross section 20 including a top portion 19 of the baffle to contact the resin layer portion side circumferential portion of the opening. If the height of the baffle from the base portion 15 to the top portion 19 is insufficient, the dialysate which has entered the housing directly collides with the hollow fiber membranes. If the height of the baffle from the base portion 15 to the top portion 19 is too great, contrary, the space between the baffle and the resin layer portion is relatively reduced, whereby most of the dialysate which has entered the housing forms a slit flow perpendicular to the hollow fiber membranes. This increases the resistance to prevent the dialysate from sufficiently reaching the center of the bundle.

The hemodialyzer preferably has a blood volume per unit membrane area as small as possible. The blood volume of the hemodialyzer accounts for half or more of the amount of blood brought out from the body during extracorporeal circulation. Accordingly, the blood volume of the hemodialyzer is preferably as small as possible. Since the blood volume is mainly determined by the inner diameter, the length, and the bundle diameter (header diameter) of the hollow fiber membranes and the internal volume of the header, it is preferable that each factor be small. However, if the inner diameter of the hollow fiber membrane or the internal volume of the header is reduced to a large extent, an increase of the pressure drop in the blood side occurs. Moreover, it is necessary to balance the length and the bundle diameter from the viewpoint of the pressure drops in blood side and dialysate side. Upon the consideration of the above factors, in the hemodialyzer with a large membrane area exceeding 2.4 $m^2$, the blood volume per unit membrane area is preferably 50 to 65 $ml/m^2$, more preferably 50 to 60 $ml/m^2$, and still more preferably 50 to 55 $ml/m^2$.

The polysulfone hemodialyzer according to the present invention has the above-described structural features. As a result, since the dialysate which has entered into the hemodialyzer reaches the center of the bundle in the dialysate rectifying portion, a maldistribution flow is significantly improved. A maldistribution flow evaluation method has been known which divides the dialysate channel inside the hemodialyzer into a plurality of portions and measures the dialysis performance in each channel unit, as disclosed in the non-patent document 1 and JP-A-2005-152295 cited in the section "BACKGROUND ART". In the present invention, the dialysate channel is divided into a center portion and eight peripheral portions (total nine portions), and the overall mass transfer coefficient is calculated from the urea partial clearance measured for each channel to evaluate. Urea is focused as the index because commercially available polysulfone hemodialyzers with a relatively large membrane area exhibit an insufficient dialysis performance for urea even though urea is the most basic uremic toxin which must be removed by the hemodialyzer.

In this evaluation method, the polysulfone hemodialyzer according to the present invention must exhibit a difference ($Ko_{(C)}-Ko_{(AVE)}$) between the urea center portion overall mass transfer coefficient ($Ko_{(C)}$) and the urea average peripheral portion overall mass transfer coefficient ($Ko_{(AVE)}$) of as small as $-2.7 \times 10^{-4}$ to $2.5 \times 10^{-4}$ cm/sec at a blood flow rate of 400 ml/min and a dialysate flow rate of 800 ml/min. The above difference is preferably a positive value including zero, i.e. 0 to $2.5 \times 10^{-4}$ cm/sec. It is also necessary that the urea overall mass transfer coefficient measured at a blood flow rate of 400 ml/min and a dialysate flow rate of 800 ml/min using a normal clearance measuring method is as high as $9.50 \times 10^{-4}$ cm/sec or more. This ensures that a low urea clearance in the center portion which has been a bottleneck heretofore is significantly improved, whereby the "high dialysis performance over a wide molecular weight range" which cannot be achieved by a known polysulfone hemodialyzer is obtained.

The term "high dialysis performance over a wide molecular weight range" used herein means that the overall mass transfer coefficient (Ko) of a solute with a molecular weight of (M) at a blood flow rate of 400 ml/min and a dialysate flow rate of 800 ml/min satisfies the following relations. In more detail, the term "high dialysis performance over a wide molecular weight range" used herein means that the overall mass transfer coefficients (Ko) of urea which is an uremic toxin with a low molecular weight of 60, vitamin $B_{12}$ which is a marker of an uremic toxin with a medium molecular weight of 1,355, and dextran T10 (molecular weight: 9,600) which is a marker of $\beta_2$-microglobulin which is an uremic toxin protein with a high molecular weight of 11,800 at a blood flow rate of 400 ml/min and a dialysate flow rate of 800 ml/min simultaneously satisfy the following inequality (4).

$$Ko > 89.313 \times M^{-0.4865} \ (60 \leq M \leq 9600) \tag{4}$$

The overall mass transfer coefficient (Ko) is given by the following equation (5).

$$Ko = [(Qb/60)/(A \times 10^4 \times (1-Z))] \times \ln\ [(1-EZ)/(1-E)] \tag{5}$$

Where,
E=CL/Qb
Z=Qb/Qd
A ($m^2$): membrane area
CL (ml/min): clearance
Qb (ml/min): blood side flow rate
Qd (ml/min): dialysate side flow rate Uremic toxins with various molecular weights from a low-molecular-weight substance to proteins are contained in the blood of a renal failure patient. These uremic toxins must also be removed in a well-balanced manner when using a hemodialyzer with a large membrane area. The dialysis conditions include generally employed basic conditions (blood flow rate=200 ml/min, dialysate flow rate=500 ml/min), high flow rate conditions (blood flow rate=200 to 400 ml/min, dialysate flow rate=500 to 800 ml/min) in which the blood flow rate and the dialysate flow rate are increased, and dialysate saving conditions (blood flow rate=300 to 400 ml/min, dialysate flow rate=500 ml/min) in which the dialysate flow rate is relatively decreased. A hemodialyzer is required to exhibit a high dialysis performance irrespective of these conditions.

The polysulfone hemodialyzer with a large membrane area according to the present invention can exhibit a high dialysis performance not only under the basic conditions but also under the high flow rate conditions and the dialysate saving conditions by having the above-described well-balanced dialysis performance. This enables the average dialysis time to be reduced from 4 to 5 hour/session under the basic conditions to about 2.5 to 3.5 hour/session. Moreover, the amount of dialysate used can be reduced. These conditions are, of course, suitable for a big physique patient who weighs more than 176 pounds and has a protein catabolic rate of 0.9 or more which requires hard treatment conditions. These conditions are more suitable for a dialysis patient who weighs more than 199 pounds and has a protein catabolic rate of 1.2 or more.

The method of manufacturing the polysulfone hemodialyzer according to the present invention is not particularly limited. The polysulfone hemodialyzer according to the present invention may be manufactured using a known method of manufacturing a hollow fiber membrane hemodialyzer disclosed in JP-A-11-90186, JP-A-2003-265934, or the like. Specifically, a tubular housing is filled with a hollow fiber membrane bundle, and a resin layer portion is formed by injecting a curable resin such as polyurethane into each end of the hollow fiber membrane bundle using a centrifugal method. After the resin has been cured, an opening for the hollow fiber membranes is formed by cutting the resin layer portion, and the cut surface is capped with a header.

In these steps, it is preferable to form the dialysate rectifying portion according to the present invention during filling the tubular housing with the bundle and forming the resin layer portion. The concrete method is not particularly limited. For example, a method of spraying air to the end face of the bundle may be suitably utilized. As the method of spraying air to the end face of the bundle, JP-A-2001-309974 discloses a method of deconcentrating the hollow fiber membranes in the bundle by spirally spraying air. However, the inventors of the present invention have found that a method of increasing the spraying pressure stepwise is more suitable for forming the dialysate rectifying portion than the above method.

In more detail, the tubular housing filled with the bundle is placed horizontally. A restriction ring corresponding to the diameter of the bundle in the resin layer portion is provided to the end portion of the bundle, and a compressed gas with a predetermined pressure is sprayed onto the end face of the bundle. In this case, 1 to 15 holes with a diameter of about 0.3 mm are formed in the side surface of a pipe with a diameter of about 1 to 3 cm, and compressed air discharged through the holes at a pressure of 0.02 MPa is sprayed onto from the lower portion to the upper portion of the end face of the hollow fiber membrane bundle for 1 to 5 seconds while moving the pipe. Then, compressed air discharged at a pressure of 0.02 MPa is sprayed onto the hollow fiber membrane bundle for 1 to 5 seconds in the same manner. The dialysate rectifying portion according to the present invention is then formed by injecting polyurethane into the end portion to form a resin layer portion and securing the bundle to the housing.

If the gas is sprayed at a low pressure at this moment, the dialysate rectifying portion is not formed. Otherwise, even if the dialysate rectifying portion is formed, the dialysate rectifying portion cannot keep its form and is deformed during centrifugation. On the other hand, If the gas is abruptly sprayed at a high pressure, the hollow fiber membranes are irregularly arranged. Therefore, if air is sprayed stepwise from a low pressure to a high pressure, the dispersibility of the hollow fiber membranes is improved even at a distance from the spraying surface while the dialysate rectifying portion is formed. This leads to an improvement in dialysis performance.

The detailed spraying conditions may be appropriately adjusted and selected depending on the properties of the hollow fiber membrane such as the material, strength, rigidity, and electrostatic properties. Specifically, the diameter, number, and pitch of holes formed in the pipe, the pressure applied to the pipe, the air spraying time, number of the air spraying, the spraying direction, the spraying distance, and the like may be optimized in order to adjust the flow rate of air to be sprayed and the like. Air may be sprayed stepwise while continuously or discontinuously changing the pressure.

The hemodialyzer thus formed is filled with an aqueous medium and capped, or in a dry state as it is, sealed in a sterilization bag, and then sterilized utilizing radiation, high-pressure steam or the like, whereby the hemodialyzer can be used as a medical hemodialyzer.

EXAMPLES

The present invention is described below in more detail by way of examples. Note that the present invention is not limited to the following examples. The measurement methods used in the examples are firstly described below.

(Clearance)

As the dialysis performance of the hemodialyzer, the urea clearance was measured in an aqueous system in accordance with the dialyzer performance evaluation criteria (Japanese Society for Artificial Organs, September, 1977). In the urea clearance measurement in an aqueous system, an aqueous solution prepared by dissolving urea in pure water to a concentration of 100 mg/dl (concentration error: ±10%) was used as a blood side liquid, and pure water was used as a dialysate side liquid. The measurement was conducted under basic conditions in which the blood side flow rate was 200 ml/min and the dialysate side flow rate was 500 ml/min, dialysate saving conditions in which the blood side flow rate was 300 to 400 ml/min and the dialysate side flow rate was 500 ml/min, and high flow rate conditions in which the blood side flow rate was 400 ml/min and the dialysate side flow rate was 800 ml/min. The urea concentration in the resulting specimen was determined by an urease-indophenol method.

The measurement was similarly conducted for vitamin $B_{12}$ at a concentration of 6 mg/dl, and the vitamin $B_{12}$ concentration in the resulting specimen was determined by an absorption spectrochemical analysis method.

The measurement was similarly conducted for dextran T10 (molecular weight: 9,600; manufactured by Pharmacia) at a concentration of 50 mg/dl, and the dextran concentration in the resulting specimen was determined by liquid chromatography using a differential refractometer.

(Partial Clearance)

As a header for partial clearance measurement, a special header was prepared in which blood outlet ports were provided at the center portion and eight locations around the center portion. The header was attached and secured to the blood outlet port side of the hemodialyzer, and the resulting hemodialyzer was used for measurement.

A circuit was basically similar to a normal clearance measurement circuit, and by providing a multiheader type pump to nine circuits connected to the blood side outlet port, the flow rate of each circuit was adjusted to became constant. In the urea partial clearance measurement, an aqueous solution prepared by dissolving urea in pure water to a concentration of 100 mg/dl (concentration error: ±10%) was used as a blood side liquid, and pure water was used as a dialysate side liquid. The temperatures of the blood side liquid and the dialysate side liquid were adjusted to 37±1° C., and the measurement was conducted at a blood side flow rate of 400 ml/min and a dialysate side flow rate of 800 ml/min. The urea concentration in the resulting specimen was determined by an urease-indophenol method.

(PVP Insolubilization Rate in Membrane)

A dried hollow fiber membrane was subjected to elemental analysis, and the total amount of PVP contained in the hollow fiber membrane was determined from the resulting nitrogen concentration.

2 ml of N-methyl-2-pyrrolidone was then added to 0.1 g of the dried hollow fiber membranes to dissolve the hollow fiber membranes. 99 ml of distilled water for injection at 55° C. was added to the resulting solution, and the mixture was stirred to precipitate the polysulfone polymer. Since PVP which was not insolubilized by crosslinking was contained in this aqueous phase, the aqueous phase was partially filtered through a microfilter to remove solids, and the PVP concentration in the aqueous solution was measured by gel permeation chromatography (GPC). The amount of water-soluble PVP per specific weight of the hollow fiber membrane was determined, and the insoluble PVP content was calculated using the following equation (6).

PVP insolubilization rate in membrane(%)=100×(total amount of PVP in membrane−total amount of water-soluble PVP)/total amount of PVP in membrane (6)

(Albumin Permeation Rate)

A circulation circuit using a bovine plasma pool (TP=6.5 g/dl, 37° C.) was formed, and the hemodialyzer was incorporated in the circuit. A filtration circuit was arranged so that the filtrate from the hemodialyzer returned to the pool. The bovine plasma was circulated at a blood side flow rate of 200 ml/min and a filtration flow rate of 10 ml/min/m² in the circuit, and the albumin concentrations in the pool liquid and the filtrate after 60 minutes of circulation were measured using a BCG method. The percentage of the albumin concentration in the filtrate with respect to the albumin concentration in the pool was taken as the permeation rate.

Example 1

A hollow fiber membrane bundle formed from polysulfone and polyvinylpyrrolidone and having 16,130 filaments and a length of 30 cm was provided referring to a known wet spinning method for a polysulfone hemodialysis membrane (WO 98/52683). The hollow fiber membrane in the bundle had a cross-sectional structure with an inner diameter of 185 μm and a thickness of 45 μm and was crimped at a pitch of 0.8 cm and an amplitude of 0.5 mm. The water permeation rate was 298 ml/mmHg·hr·m².

A tubular housing, of which the minimum inner diameter of the body portion was 45.9 mm, the inner diameter of the housing at the diameter-expansion-start surface was 46.2 mm, and the length of the straight portion was 220 mm and which had a peripheral type baffle with a height of 6 mm at the boundary between the body portion and the head portion, was filled with the bundle. A restriction ring with an inner diameter of 57 mm was secured to the end portion of the tubular housing. A dispersion pipe with a diameter of about 1.5 cm in which 15 holes with a diameter of 0.3 mm were formed at intervals of 5 mm was placed at a position 5 cm from the end face. The pipe was moved from the lower portion to the upper portion of the end face of the bundle while spraying compressed air at 0.02 MPa from the holes. After performing the first spraying for five seconds, compressed air at 0.2 MPa was sprayed for two seconds as the second spraying. A dialysate rectifying portion was formed on each end of the bundle by this processing.

A resin layer portion was then formed by injecting a polyurethane resin into the end portion of the bundle by centrifugal molding, and the cured resin layer portion was sliced to form an open end for the hollow fiber membranes. A header was capped over the cut surface of the semifinished product and secured to obtain a hemodialyzer with a membrane area of 2.5 m². Tables 1 and 3 show the specification of the hemodialyzer.

The resulting hemodialyzer was partially disassembled and subjected to dimensional measurement. It was confirmed that a dialysate rectifying portion with a dialysate channel ratio of 0.31 and a length of 13 mm was formed.

Example 2

A hemodialyzer was prepared in the same manner as in Example 1 except for using a restriction ring with an inner diameter of 47 mm. A dialysate rectifying portion with a dialysate channel ratio of 0.40 and a length of 13 mm was formed in the resulting hemodialyzer.

Example 3

A hemodialyzer was prepared in the same manner as in Example 1 except for performing the second spraying for five seconds when spraying compressed air. A dialysate rectifying portion with a dialysate channel ratio of 0.31 and a length of 27 mm was formed in the resulting hemodialyzer.

Example 4

A hemodialyzer was prepared in the same manner as in Example 3 except for using a restriction ring with an inner diameter of 47 mm. A dialysate rectifying portion with a dialysate channel ratio of 0.40 and a length of 27 mm was formed in the resulting hemodialyzer.

Example 5

A hollow fiber membrane bundle formed from polysulfone and polyvinylpyrrolidone and having 16,400 filaments and a length of 30 cm was provided. In this step, since the amount of raw solution discharged from the spinning nozzle and the composition of the hollow-forming agent were changed and crimp-forming gear was not used, the resulting hollow fiber membrane was a straight fiber having a cross-sectional structure with an inner diameter of 182 μm and a membrane thickness of 42 μm. The water permeation rate was 347 ml/mmHg·hr·m².

A hemodialyzer was prepared in the same manner as in Example 1 except for using the above hollow fiber membrane bundle and a restriction ring with an inner diameter of 50 mm and spraying compressed air at 0.1 MPa for five seconds as the second spraying when spraying compressed air. A dialysate rectifying portion with a dialysate channel ratio of 0.36 and a length of 27 mm was formed in the resulting hemodialyzer.

Example 6

A hemodialyzer, in which the bundle filling rate in the portion of the housing having the minimum inner diameter was 68%, was prepared in the same manner as in Example 1 except for using a tubular housing with a minimum inner diameter of the body portion of 39.2 mm and an inner diameter of the housing at the diameter-expansion-start surface of 39.4 mm and a restriction ring with an inner diameter of 54 mm. A dialysate rectifying portion with a dialysate channel ratio of 0.33 and a length of 27 mm was formed in the resulting hemodialyzer.

Example 7

A hemodialyzer with a membrane area of 3.2 m² was prepared in the same manner as in Example 1 except for using a bundle with 20,650 filaments, a tubular housing with a minimum inner diameter of the body portion of 58.8 mm and an inner diameter of the housing at the diameter-expansion-start surface of 59.1 mm, and a restriction ring with an inner diameter of 67 mm. A dialysate rectifying portion with a dialysate channel ratio of 0.35 and a length of 27 mm was formed in the resulting hemodialyzer.

Example 8

A tubular housing, of which the minimum inner diameter of the body portion was 45.9 mm, the inner diameter of the housing at the diameter-expansion-start surface was 46.2 mm, and the length of the straight portion was 220 mm, with a peripheral type baffle at the boundary between the body portion and the head portion was filled with a same bundle as used in Example 1. The housing used in this example was a type which was not provided with a groove located between the base portion of the baffle and the open circle of the dialysate inlet port and retaining dialysate, as shown in FIG. 4(b), and in which the diameter of the baffle was increased from the base portion toward the top portion and a slope portion with a length of 11 mm was formed between the body portion and the head portion.

A restriction ring with an inner diameter of 52 mm was provided to the end portion. After spraying compressed air at 0.02 MPa for five seconds, compressed air at 0.15 MPa was sprayed for three seconds as the second spraying. After forming a resin layer portion, the cut surface was capped with a header.

The blood side and the dialysate side of the hemodialyzer were filled with an aqueous solution containing 600 ppm of sodium sulfite, and the hemodialyzer was capped. The hemodialyzer was then sterilized by applying γ-rays at 25 kGy to obtain a sterilized hemodialyzer. A dialysate rectifying portion with a dialysate channel ratio of 0.35 and a length of 27 mm was formed in the resulting hemodialyzer.

Example 9

A hollow fiber membrane bundle formed from polysulfone and polyvinylpyrrolidone and having 16,400 filaments and a length of 30 cm was provided. The hollow fiber membrane in the bundle had a cross-sectional structure with an inner diameter of 182 μm and a membrane thickness of 42 μm and was crimped at a pitch of 0.6 cm and an amplitude of 0.5 mm. The water permeation rate was 347 ml/mmHg·hr·m².

A sterilized hemodialyzer with a filling rate of 64% was prepared in the same manner as in Example 8 except for using the above hollow fiber membrane bundle, a housing having the slope portion with a length of 13 mm, and a restriction ring with an inner diameter of 52 mm. A dialysate rectifying portion with a dialysate channel ratio of 0.35 and a length of 27 mm was formed in the resulting hemodialyzer.

Comparative Example 1

A hemodialyzer was prepared in the same manner as in Example 1 except that compressed air was not sprayed onto the end portion of the bundle after providing a restriction ring with an inner diameter of 46 mm. A dialysate rectifying portion was not formed in the resulting hemodialyzer.

Comparative Example 2

A hemodialyzer was prepared in the same manner as in Example 1 except for using a tubular housing, of which the length from the diameter-expansion-start surface (i.e. top portion of the baffle) to the end of the head portion was 50 mm, and a restriction ring with an inner diameter of 48 mm. A dialysate rectifying portion with a dialysate channel ratio of 0.55 and a length of 45 mm was formed in the resulting hemodialyzer.

Comparative Example 3

A hemodialyzer was prepared in the same manner as in Example 1 except for using a tubular housing, of which the length from the diameter-expansion-start surface (i.e. top portion of the encircling baffle) to the end of the head portion was 50 mm, and a restriction ring with an inner diameter of 71 mm. A dialysate rectifying portion with a dialysate channel ratio of 0.15 and a length of 45 mm was formed in the resulting hemodialyzer.

Comparative Example 4

A hemodialyzer was prepared in the same manner as in Example 1 except for using a restriction ring with an inner diameter of 71 mm and increasing the injection amount of urethane twice. A dialysate rectifying portion with a dialysate channel ratio of 0.15 and a length of 9 mm was formed in the resulting hemodialyzer.

Reference Example 1

The above items were evaluated using a commercially available polysulfone hemodialyzer (FPX180; manufactured by Fresenius). A dialysate rectifying portion was not formed in this hemodialyzer.

Reference Example 2

The above items were evaluated using a commercially available polysulfone hemodialyzer (Toraysulfone TS-1.6UL; manufactured by Toray Industries Inc.). A dialysate rectifying portion was not formed in this hemodialyzer.

Table 1 shows the specifications and the dialysis performance of the hemodialyzers used in the examples, and Table 3 shows the specifications and the dialysis performance of the hemodialyzers used in the comparative examples. Tables 3 and 4 show the dialysis performance of these hemodialyzers.

As is clear from the comparison between Examples 1 to 4 and Comparative Examples 1 to 4, it was found that the urea clearance is improved by providing the dialysate rectifying portion in the end portion of the bundle, and the difference between the average clearance in the peripheral portions and the clearance in the center portion of the hemodialyzer is significantly reduced. It was also found that there are suitable ranges for the dialysate rectifying portion in terms of the dialysate channel diameter ratio and the total length. As is clear from Examples 5 to 9, it was found that the dialysis performance is further improved by crimping the hollow fiber membranes, partially insolubilizing PVP in the membrane, or optimizing the filling rate or the shape of the baffle. This improves the effects of the dialysate rectifying portion according to the present invention.

As is clear from the comparison between Examples 8 and 9 and the reference examples, since a high dialysis performance is obtained by providing the dialysate rectifying portion in the end portion of the bundle, a high urea clearance is obtained in the examples in comparison with the reference examples. In particular in Example 9, even if the dialysate flow rate is reduced from 500 ml/min to 400 ml/min, since the urea clearance becomes 200 ml/min when the blood flow rate is 200 ml/min, a dialysis efficiency of 100% is obtained though the dialysate flow rate is reduced by 20%. Specifically, the dialysate can be saved.

Table 4 shows the dialysis performance for a solute having each molecular weight measured for Examples 8 and 9, Comparative Example 1, and Reference Example 1. As is clear from the comparison between the examples and the comparative example, it was found that the hemodialyzer according to the present invention exhibits an excellent dialysis performance over a wide molecular weight range.

TABLE 1

| | | Example 1 | Example 2 | Example 3 | Example 4 | Example 5 | Example 6 | Example 7 | Example 8 | Example 9 |
|---|---|---|---|---|---|---|---|---|---|---|
| Hollow fiber membrane | Number of membranes | 16130 | ← | ← | ← | 16400 | 16130 | 20646 | 16130 | 16450 |
| | Shape | Crimped | ← | ← | ← | Straight | Crimped | ← | ← | ← |
| | Pitch (cm) | 0.8 | ← | ← | ← | — | 0.8 | ← | ← | 0.6 |
| | Amplitude (mm) | 0.5 | ← | ← | ← | 0.5 | ← | ← | ← | 0.5 |
| | Inner diameter (μm) | 185 | ← | ← | ← | 182 | 185 | ← | ← | 182 |
| | Thickness (μm) | 45 | ← | ← | ← | 42 | 45 | ← | ← | 42 |
| | Water permeation rate (ml/m2·hr·mmHg) | 298 | ← | ← | ← | 347 | 298 | ← | ← | 347 |
| | PVP insolubilization rate (%) | 0 | ← | ← | ← | ← | ← | ← | 75 | 70 |
| Bundle | Dialysate rectifying portion | Provided | ← | ← | ← | ← | ← | ← | ← | ← |
| | Dialysate channel diameter ratio | 0.31 | 0.40 | 0.31 | 0.40 | 0.36 | 0.33 | 0.35 | 0.35 | 0.35 |
| | Length (mm) | 13 | 13 | 27 | 27 | 27 | 27 | 27 | 27 | 27 |
| | Bundle diameter in resin layer portion (mm) | 57 | 47 | 57 | 47 | 50 | 54 | 67 | 52 | 52 |
| | Length of straight portion/length of rectifying portion | 18.5 | ← | ← | ← | 7.9 | 7.9 | ← | ← | ← |
| | Filling rate (%) | 58 | ← | ← | ← | 64 | 68 | 58 | ← | 64 |
| | Membrane area (m$^2$) | 2.5 | ← | ← | ← | ← | 2.5 | 3.2 | 2.5 | ← |
| Housing | Minimum inner diameter of housing body portion (mm) | 45.9 | ← | ← | ← | ← | 39.2 | 58.8 | 45.9 | ← |
| | Inner diameter of housing at diameter-expansion-start surface (mm) | 46.2 | ← | ← | ← | ← | 39.4 | 59.1 | 46.2 | ← |
| | Length of straight portion (mm) | 220 | ← | ← | ← | ← | ← | ← | ← | ← |
| | Baffle | Peripheral | ← | ← | ← | ← | ← | ← | Peripheral diameter expansion | ← |
| | Length of slope portion | 0 | ← | ← | ← | ← | ← | ← | 11 | 13 |
| | Blood volume (ml/m$^2$) | 51 | ← | 55 | 49 | 53 | 51 | 60 | 51 | ← |
| Urea clearance (ml/min) | | 367 | 365 | 369 | 371 | 365 | 400 | 400 | 379 | 391 |
| Urea overall mass transfer coefficient Ko (×10$^{-4}$ cm/sec) | | 10.03 | 9.74 | 10.34 | 10.67 | 9.70 | 77.4 | 77.4 | 12.3 | 16.70 |
| Urea center portion clearance (ml/min) | | 366 | 365 | 368 | 372 | 366 | 398 | 399 | 380 | 390 |

TABLE 1-continued

|  | Example 1 | Example 2 | Example 3 | Example 4 | Example 5 | Example 6 | Example 7 | Example 8 | Example 9 |
|---|---|---|---|---|---|---|---|---|---|
| Average peripheral portion clearance (ml/min) | 379 | 375 | 373 | 372 | 380 | 394 | 395 | 372 | 385 |
| Urea center portion clearance − average peripheral portion clearance (ml/min) | −13 | −10 | −5 | 0 | −14 | 4 | 4 | 8 | 5 |
| Urea center portion $Ko_{(c)}$ − peripheral portion $KO_{(AVE)}$ ($\times 10^{-4}$ cm/sec) | −2.41 | −1.67 | −0.84 | 0 | −2.66 | 0.97 | 1.48 | 1.69 | 2.10 |

TABLE 2

|  |  | Comparative Example 1 | Comparative Example 2 | Comparative Example 3 | Comparative Example 4 | Reference Example 1 | Reference Example 2 |
|---|---|---|---|---|---|---|---|
| Hollow fiber membrane | Number of membranes | 16130 | ← | ← | ← | Not measured | Not measured |
|  | Shape | Crimped | ← | ← | ← | Crimped | Spacer |
|  | Pitch (cm) | 0.8 | ← | ← | ← | 0.4 | 1 |
|  | Amplitude (mm) | 0.5 | ← | ← | ← | 0.5 | 0.8 |
|  | Inner diameter (μm) | 185 | ← | ← | ← | 195 | 200 |
|  | Thickness (μm) | 45 | ← | ← | ← | 45 | 45 |
|  | Water permeation rate (ml/m2 · hr · mmHg) | 298 | ← | ← | ← | 180 | 934 |
|  | PVP insolubilization rate (%) | 0 | ← | ← | ← | 0 | 99 |
| Bundle | Dialysate rectifying portion | Not provided | Provided | ← | ← | Not provided | ← |
|  | Dialysate channel diameter ratio | 1.00 | 0.55 | 0.15 | 0.15 | — | — |
|  | Length (mm) | 0 | 45 | 45 | 9 | — | — |
|  | Bundle diameter in resin layer portion (mm) | 46 | 48 | 71 | 71 | — | — |
|  | Length of straight portion/ length of rectifying portion | 18.5 | 3.9 | 3.9 | 42.3 | — | — |
|  | Filling rate (%) | 58 | ← | ← | ← | 57 | 56 |
|  | Membrane area (m²) | 2.5 | ← | ← | ← | 2.0 | 1.6 |
| Housing | Minimum inner diameter of housing body portion (mm) | 45.9 | ← | ← | ← | — | — |
|  | Inner diameter of housing at diameter-expansion-start surface (mm) | 46.2 | ← | ← | ← | — | — |
|  | Length of straight portion (mm) | 220 | ← | ← | ← | — | — |
|  | Baffle | Peripheral | ← | ← | ← | Tongue | Peripheral slit |
|  | Length of slope portion | 0 | ← | ← | ← | — | — |
|  | Blood volume (ml/m²) | 51 | ← | 55 | 49 | 58 | 53 |
| Urea clearance (ml/min) |  | 335 | 340 | 341 | 345 | 338 | 360.4 |
| Urea overall mass transfer coefficient Ko ($\times 10^{-4}$ cm/sec) |  | 6.80 | 7.20 | 7.20 | 7.60 | 7.00 | 9.10 |
| Urea center portion clearance (ml/min) |  | 333 | 341 | 340 | 343 | 339 | 360 |
| Average peripheral portion clearance (ml/min) |  | 391 | 375 | 342 | 354 | 374 | 376 |
| Urea center portion clearance − average peripheral portion clearance (ml/min) |  | −58 | −34 | −2 | −11 | −35 | −16 |
| Urea centerportion $Ko_{(c)}$ − peripheral portion $KO_{(AVE)}$ ($\times 10^{-4}$ cm/sec) |  | −10.00 | −4.17 | −0.16 | −1.01 | −4.13 | −2.53 |

TABLE 3

| Overall mass transfer coefficient (Ko) (cm/sec) | Example 8 | Example 9 | Comparative Example 1 | Reference Example 1 |
|---|---|---|---|---|
| Urea | $12.30 \times 10^{-4}$ | $16.67 \times 10^{-4}$ | $6.80 \times 10^{-4}$ | $11.57 \times 10^{-4}$ |
| Vitamin B12 | $3.26 \times 10^{-4}$ | $3.56 \times 10^{-4}$ | $2.91 \times 10^{-4}$ | $3.06 \times 10^{-4}$ |
| Dextran | $1.21 \times 10^{-4}$ | $1.32 \times 10^{-4}$ | $1.03 \times 10^{-4}$ | $0.95 \times 10^{-4}$ |

Blood flow rate = 400 ml/min, dialysate flow rate = 800 ml/min

TABLE 4

|  | Example 8 | Example 9 | Comparative Example 1 | Reference Example 1 |
|---|---|---|---|---|
| Urea clearance (ml/min) | | | | |
| Blood flow rate = 200 ml/min Dialysate flow rate = 300 ml/min | 186.6 | 195 | 179.3 | 182.2 |
| Blood flow rate = 200 ml/min Dialysate flow rate = 400 ml/min | 193.4 | 200 | 188.4 | 189.5 |
| Blood flow rate = 200 ml/min Dialysate flow rate = 500 ml/min | 195.6 | 200 | 189.7 | 191.4 |
| Urea overall mass transfer coefficient (Ko) (cm/sec) | | | | |
| Blood flow rate = 200 ml/min Dialysate flow rate = 300 ml/min | $5.83 \times 10^{-4}$ | $8.89 \times 10^{-4}$ | $4.57 \times 10^{-4}$ | $5.00 \times 10^{-4}$ |
| Blood flow rate = 200 ml/min Dialysate flow rate = 400 ml/min | $12.22 \times 10^{-4}$ | $25.59 \times 10^{-4}$ | $9.82 \times 10^{-4}$ | $8.54 \times 10^{-4}$ |
| Blood flow rate = 200 ml/min Dialysate flow rate = 500 ml/min | $18.45 \times 10^{-4}$ | $26.26 \times 10^{-4}$ | $13.83 \times 10^{-4}$ | $9.87 \times 10^{-4}$ |

The overall mass transfer coefficient was calculated from the clearance of Example 9 taking the clearance of 200 as 199.9999.

INDUSTRIAL APPLICABILITY

The polysulfone hemodialyzer according to the present invention can exhibit a high dialysis performance than conventional polysulfone hemodialyzer over a wide molecular weight range from urea with a low molecular weight to $\beta_2$-microglobulin with a high molecular weight, though the polysulfone hemodialyzer has a large membrane area exceeding 2.4 m². Since the polysulfone hemodialyzer according to the present invention can exhibit a high dialysis performance without requiring an additional structural member or additional structural treatment such as a spacer fiber or crimping or a complicated housing structure such as a slit baffle, the polysulfone hemodialyzer is useful for hemodialysis or hemodiafiltration using a dialysate.

Since the polysulfone hemodialyzer according to the present invention has a large membrane area in comparison with a known polysulfone hemodialyzer, the polysulfone hemodialyzer according to the present invention is suitable for treating a big physique patient who weighs more than 176 pounds, for example. Moreover, desired treatment effects can be obtained in shorter period of time by carrying out dialysis under the condition of higher blood flow rate and higher dialysate flow rate than conventional. Therefore, such a high treatment efficiency improves the quality of life (QOL) of the patient. Moreover, since the bed turnover rate for dialysis can be increased by using such a hemodialyzer, the polysulfone hemodialyzer according to the present invention is useful for dialysis management.

The invention claimed is:

1. A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped,
wherein the hemodialyzer has a membrane area of more than 2.4 m² and 3.2 m² or less, and the bundle includes a straight portion and a dialysate rectifying portion, a ratio of a dialysate channel area in a diameter-expansion-start portion to a dialysate channel area inside the resin layer portion is 0.2 to 0.5, and the dialysate rectifying portion having a distance from the diameter-expansion-start portion to the inside of the resin layer portion of 10 to 46 mm is provided in a dialysate inlet port side end portion of the bundle,
wherein a filling rate of the bundle with respect to the minimum diameter of the body portion of the housing is 55% or more and less than 69%.

2. The polysulfone hemodialyzer according to claim 1, wherein a ratio of a length of the straight portion of the hollow fiber membrane bundle to a length of the dialysate rectifying portion on the dialysate inlet port side is 3.0 to 10.0.

3. The polysulfone hemodialyzer according to claim 1, wherein the bundle includes crimped hollow fiber membranes or hollow fiber membranes provided with spacer fibers wound therearound.

4. The polysulfone hemodialyzer according to claim 1, wherein the hollow fiber membranes have an inner diameter of 170 to 190 μm and a thickness of 25 to 50 μm.

5. The polysulfone hemodialyzer according to claim 1, wherein the hollow fiber membranes have a water permeation rate of 100 to 350 ml/m²·hr·mmHg.

6. The polysulfone hemodialyzer according to claim 1, wherein 50 to 95 wt % of the polyvinylpyrrolidone included in the hollow fiber membranes is crosslinked and water-insolubilized.

7. The polysulfone hemodialyzer according to claim 1, wherein a peripheral type baffle is provided in the dialysate inlet port side head portion of the housing and is gradually increased in diameter along the shape of the dialysate rectifying portion.

8. The polysulfone hemodialyzer according to claim 7, wherein the peripheral type baffle is a slit baffle of which the entire circumference of its top portion reaches the resin layer portion.

9. The polysulfone hemodialyzer according to claim 7, wherein the peripheral type baffle has a base portion at a boundary between the body portion and the head portion of the housing and of which a virtual cross section including the base portion is positioned to contact the body portion side circumferential portion of an opening of the dialysate inlet port.

10. The polysulfone hemodialyzer according to claim 1, wherein a slope portion is provided between the body portion and the head portion of the tubular housing along the outer circumference of the dialysate rectifying portion of the bundle.

11. The polysulfone hemodialyzer according to claim 1, having a blood volume per unit membrane area of 50 to 65 ml/m$^2$.

12. The polysulfone hemodialyzer according to claim 1, having a urea overall mass transfer coefficient of $9.50 \times 10^{-4}$ cm/sec or more at a blood flow rate of 400 ml/min and a dialysate flow rate of 800 ml/min, and a difference ($Ko_{(C)} - Ko_{(AVE)}$) between a urea center portion overall mass transfer coefficient ($Ko_{(C)}$) and an average urea peripheral portion overall mass transfer coefficient ($Ko_{(AVE)}$) at a blood flow rate of 400 ml/min and a dialysate flow rate of 800 ml/min of $-2.7 \times 10^{-4}$ to $2.5 \times 10^{-4}$ cm/sec.

13. A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped, wherein the hemodialyzer has a membrane area of more than 2.4 m$^2$ and 3.2 m$^2$ or less, and a urea overall mass transfer coefficient is $9.50 \times 10^{-4}$ cm/sec or more at a blood flow rate of 400 ml/min and a dialysate flow rate of 800 ml/min, and a difference ($Ko_{(C)} - Ko_{(AVE)}$) between a urea center portion overall mass transfer coefficient ($Ko_{(C)}$) and an average urea peripheral portion overall mass transfer coefficient ($Ko_{(AVE)}$) at a blood flow rate of 400 ml/min and a dialysate flow rate of 800 ml/min is $-2.7 \times 10^{-4}$ to $2.5 \times 10^{-4}$ cm/sec, wherein a filling rate of the bundle with respect to the minimum diameter of the body portion of the housing is 55% or more and less than 69%.

14. A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped, wherein the hemodialyzer has a membrane area of more than 2.4 m$^2$ and 3.2 m$^2$ or less, and an overall mass transfer coefficient (Ko) of a solute with a molecular weight (M) at a blood flow rate of 400 ml/min and a dialysate flow rate of 800 ml/min satisfies the following relational, $$Ko > 89.313 \times M^{-0.4865} \ (60 \leq M < 9600), \text{ and}$$

wherein a filling rate of the bundle with respect to the minimum diameter of the body portion of the housing is 55% or more and less than 69%.

15. A polysulfone hemodialyzer comprising a tubular housing having a body portion and head portions and providing a dialysate inlet port in one of the head portions and a dialysate outlet port in the other head portion, a hollow fiber membrane bundle which is formed from a polysulfone polymer and polyvinylpyrrolidone and filled in the tubular housing, a resin layer portion provided on an end of the head portion of the housing, securing the bundle in the housing and forming an open end for the hollow fiber membranes, and a header portion which has a blood circulation port and with which the resin layer portion is capped, wherein the hemodialyzer has a membrane area of more than 2.4 m$^2$ and 3.2 m$^2$ or less, and the bundle includes a straight portion and a dialysate rectifying portion, and the dialysate rectifying portion having a distance from the diameter-expansion-start portion to the inside of the resin layer portion of 10 to 46 mm is provided in a dialysate inlet port side end portion of the bundle, wherein a filling rate of the bundle with respect to the minimum diameter of the body portion of the housing is 55% or more and less than 69%.

16. The polysulfone hemodialyzer according to claim 1, wherein the filling rate of the bundle is less than 68%.

17. The polysulfone hemodialyzer according to claim 1, wherein the filling rate of the bundle is less than 64%.

* * * * *